(12) United States Patent  
Gharib

(10) Patent No.: US 6,679,687 B2
(45) Date of Patent: *Jan. 20, 2004

(54) HYDRO ELASTIC PUMP WHICH PUMPS USING NON-ROTARY BLADELESS AND VALVELESS OPERATIONS

(75) Inventor: Morteza Gharib, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,569

(22) Filed: Jul. 3, 2001

(65) Prior Publication Data

US 2001/0046445 A1 Nov. 29, 2001

Related U.S. Application Data

(63) Continuation of application No. 09/552,253, filed on Apr. 18, 2000, now Pat. No. 6,254,355.
(60) Provisional application No. 60/130,408, filed on Apr. 19, 1999.

(51) Int. Cl.⁷ ................................................ F04B 43/08
(52) U.S. Cl. .......................................... 417/474; 92/90
(58) Field of Search .............................. 417/474; 92/90, 92/91, 92

(56) References Cited

U.S. PATENT DOCUMENTS

| | | | |
|---|---|---|---|
| 2,888,877 A | * | 1/1959 | Shellman et al. ........... 417/474 |
| 3,304,386 A | * | 2/1967 | Shlesinger, Jr. ................. 92/92 |
| 3,349,716 A | * | 10/1967 | Weber ........................ 417/474 |
| 3,749,290 A | | 7/1973 | Micallef |
| 4,014,318 A | | 3/1977 | Dockum et al. |
| 4,199,083 A | | 4/1980 | LoMaglio |
| 5,033,943 A | | 7/1991 | Durrum et al. |
| 5,431,634 A | | 7/1995 | Brown |
| 5,486,099 A | | 1/1996 | Montoya |
| 5,573,384 A | * | 11/1996 | Ernsberger ................. 417/392 |

FOREIGN PATENT DOCUMENTS

| FR | 2 309 206 | 11/1976 |
|---|---|---|
| GB | 597 046 | 1/1948 |

* cited by examiner

Primary Examiner—Charles G. Freay
(74) Attorney, Agent, or Firm—Fish & Richardson P.C.

(57) ABSTRACT

A pump formed from an asymmetric tube, which is pinched to form asymmetric forces, that pump fluid.

5 Claims, 2 Drawing Sheets

HYDRO ELASTIC PUMP WHICH PUMPS USING NON-ROTARY BLADELESS AND VALVELESS OPERATIONS

This application is a continuation of U.S. application Ser. No. 09/552,253, filed on Apr. 18, 2000, now U.S. Pat. No. 6,254,355, issued on Jul. 3, 2001, which claims the benefit of provisional U.S. application Ser. No. 60/130,408, filed Apr. 19, 1999, both of which are incorporated herein by reference.

BACKGROUND

Many different pump systems are known. A typical pump uses an impeller, which spins to push a flow of fluid in a direction. Less conventional pump designs are also known, and are used in places where the fluid can actually be damaged. For example, the pumping of red blood cells may require special considerations, e.g., care to avoid damaging the red blood cells.

SUMMARY

The present application uses the concept of hydro elastic operations to form a pump.

First and second elastic chambers are used to deliver a pumping action using a pressure head difference. The pumping action occurs in either forward or backward directions depending on the way in which the element is actuated.

This pump may operate without valves. It can operate in either an open or closed loop flow system. The system describes valveless and bladeless pumping of fluids in either steady or pulsatile mode. The application also describes applications of this pump, including operation for blood pumping, a specific operation for assisting the heart in series or parallel arrangements, such as a left ventricle assist device (LVAD) or as in-phase or counter pulsating device and any other medical application such as a venous pump.

BRIEF DESCRIPTION OF THE DRAWINGS

These and other aspects will now be described in detail with respect to the accompanying drawings, wherein.

DETAILED DESCRIPTION

Figure 1:
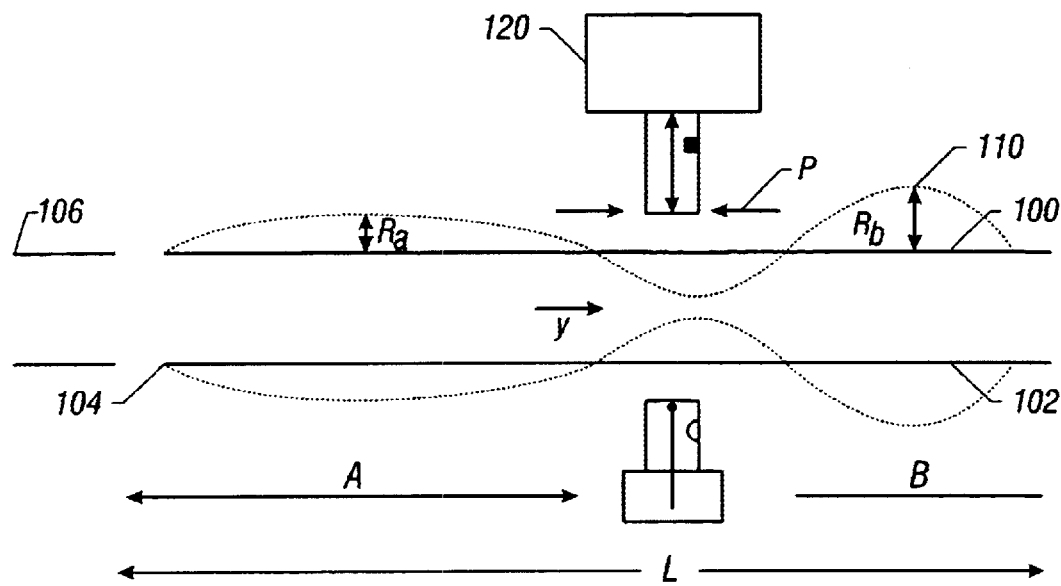
FIG. 1 shows the basic pump.

The basic pump is shown in FIG. 1. An elastic tube 100 is shown in unbroken lines. The elastic tube has a length L from end to end. This tube can be connected at each of its two ends 102 and 104 to tubes such as 106. The tubes 106 can be of any type or shape.

The elastic tube 100 is divided into three segments, labeled A, P and B. Segment P is situated between segments A and B. FIG. 1 shows Segment P situated to provide an asymmetric fluidic characteristic. In FIG. 1, the asymmetric characteristic is geometric arrangement. As shown, the length of A is not equal to the length of B. Alternatively, the length of A can be equal to the length of B, but the elasticity or diameter of the two segments may be different from one another. This is done, to allow the pumping action to materialize.

Figure 5:
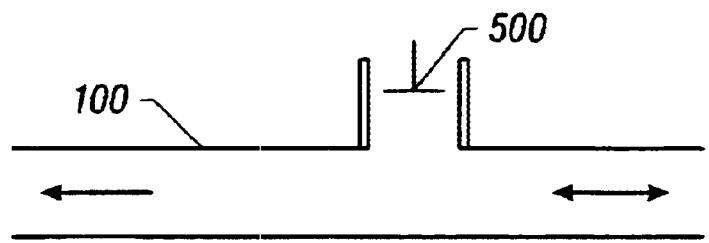
FIG. 5 shows an alternative volume reduction embodiment.

Segment P 120 provides a means of compressing the diameter of segment P to reduce its volume. The pinching can be a partial obstruction or a complete obstruction. FIG. 1 shows the compression being partial; distorting the tube to the area shown as dashed lines 110. In this respect, segment P can be a separately attached element configured in a "T" shaped piston/cylinder arrangement 500, attached to the tube 100, such as shown in FIG. 5.

When segment P is compressed, the volume within segment P is displaced to the segments A and B. This causes a rapid expansion of the volumes in A and B as shown by the line 110. Similarly, for the "T" shaped piston/cylinder arrangement, the stroke of the piston displaces the volume in section P to sections A and B.

Since the segment B is shorter than segment A, the volume expansion in segment B is more than the volume expansion in segment A. Since the same volume has been added to segments A and B, the cross-sectional radius ($R_a$) of segment A will be smaller than the corresponding radius ($R_b$) for segment B. The pressure inside each of these elastic containers varies with the inverse of the cross-sectional radius of the curvature of the elastic tubes, by virtue of the Laplace-Young law of elasticity, $$P=2\sigma/R$$

here P is the pressure, s is the surface stress and R is the cross-sectional radius of curvature.

Therefore, liquid inside segment A will actually experience more pressure from the contracting force of the elastic tube wall. While this effect is counterintuitive, it is often experienced when blowing up a balloon. The beginning portions of blowing up the balloon are much more difficult than the ending portions. The same effect occurs in the asymmetric tube. The pressure in segment A will actually be larger than the pressure in segment B.

If the constriction of segment P is removed rapidly, before the pressures in segment A and B equalize with the total system pressure, then the liquid in the high pressure section A will flow toward the low pressure segment B. Hence, liquid flows from segment A towards segment B in order to equalize pressure. This creates a pumping effect shown by the arrow y in FIG. 1.

The above has described the timing and frequency of the pinching process. This timing and frequency can be adjusted to control the volume flux as well as the direction of the flow. In addition, the size of the displaced volume depends on the relative size of segment P to the size of segments A and B. The ratios of P to A as well as the timing and frequency of the pinching may be used set various characteristics of the pump. For example, a 5 cm long tube of 1 cm in diameter can be divided to segments A=1 cm, P=1 cm and B=3 cb. At a frequency of 2 Hz and duty cycle of %20 (close to open ratio), this tube can pump up to 1.8 lit/min.

Figure 2:
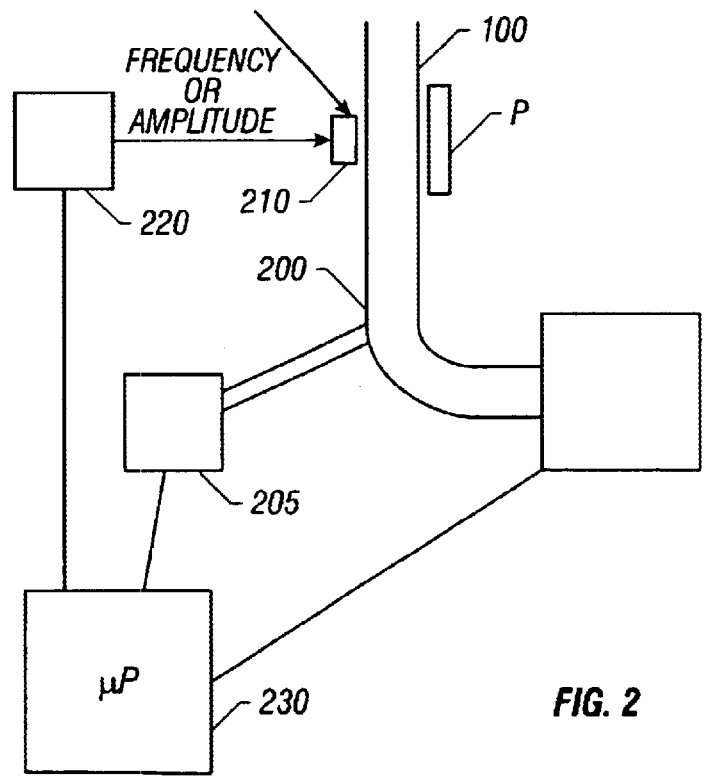
FIG. 2 shows a block diagram of the pump system in operation.

FIG. 2 shows the pump with a circuit and feedback system. In this embodiment, the pump tube 100 has less elasticity than the remainder of the system. The pipes 200, as described herein, can be the pipes through which the fluid is flowing, such as body cavity, e.g. the aorta.

The feedback system includes a flow and pressure sensor 205. The pinching element 210 is driven by a programmable driver 220 which also provides an output indicative of at least one of frequency, phase and amplitude of the driving. The values are provided to a processing element 230, which controls the timing and/or amplitude of the pinching via feedback. The relationship between timing, frequency and displacement volume for the compression cycle can be used to deliver the required performance. The parameters A, B and P; as well as the tube diameter, its elasticity and its relative elasticity, that is, relative to the elasticity of the pipes into which fluid is being pumped, can all be controlled for the desired effect. These effects can be determined by trial and error, for example. For the clinical applications, one can use the given patient's variables and find the pump parameters that are based on the patient's information.

Figure 3:
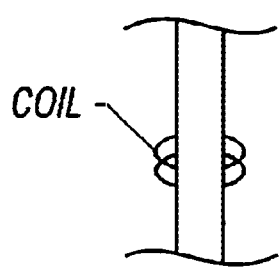
FIG. 3 shows an alternative mode.

FIG. 2 shows the actuating system for the compressing process being based on a linear translation system that sandwiches the segment P. Other translation systems—including pneumatic, hydraulic, magnetic solenoid, or an electrical stepper or DC motor can also be used. The pseudo electrical effect could be used. The effect of contractility of skeletal muscles based on polymers or magnetic fluids, or grown heart muscle tissue can also be used. The system may use a dynamic sandwiching of the segments. However, it is also possible to use a coil only around the segment as shown in FIG. 3.

Figure 4:
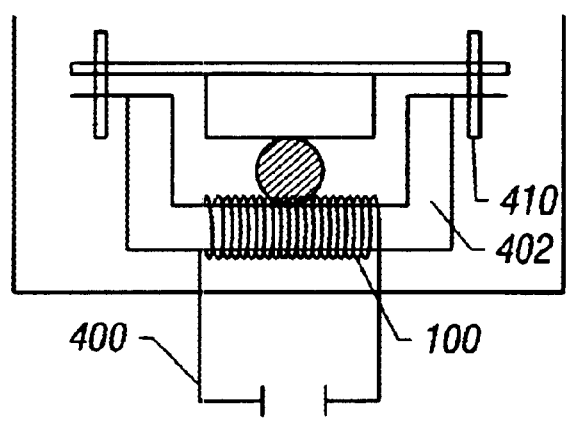
FIG. 4 shows a pinching device.

FIG. 4 shows a system where a magnet 400 has a substantially U-shaped yoke that provides a magnetic force that pulls the pincher element 405 on bearings 410. This system can be advantageous, for many reasons. The bearings 410 can be formed in a simple and reliable way, since they only require back and forth motion. They can be spring-biased. Alternatively, they can operate without spring bias. In addition, if the plunger element 405 is nonmagnetic, then the magnetic force is between the end of yoke 415 and its attractive element 420. When this happens, no magnetic force is provided through the tube 100.

A number of different alternatives are also contemplated and are described herein. In addition, a number of improvements are expected. This system can be used for pumping blood. In contrast with existing blood flow systems, such as those used in traditional left ventricle devices, this system does not require any valve at all, and certainly not the complicated one-way valve systems which are necessary in existing devices. This can provide a more reliable device, since any mechanical constrictions in the blood stream provide a potential site for mechanical failure as well as sedimentation of blood and thrombosis. Hence, this system, which does not require a valve system, can be highly advantageous.

In addition, the compression frequencies of this system can operate below 5 cycles per second. This has an advantage over modern blood pumps that may require up to 90000 rotations per minute/1500 cycles per second of up to 16 blades to propel the blood.

Unlike peristaltic pumps, this pump does not necessarily implement complete squeezing or forward displacing by a squeezing action. Complete squeezing might introduce thromboginity. In addition, when used with live animals, the lack of complete squeezing means that any organism smaller than the smallest opening will likely be unharmed by any operation of the pump.

The system also does not require any permanent constrictions such as hinges, bearings and struts. This therefore provides an improved "wash out" condition. Again, such a condition can avoid problems such as thrombosis. The elastic energy storage concept can be extremely efficient, and can be used for total implantibility in human body possibly driven by a natural energy resource such as body heat and muscle action. Implanted or external elements based on the Peltier effect can be used to convert the body heat to the electricity needed to drive the pump. Also, mechanical to electrical energy converters based on piezo-electric elements, for example can be used to harvest mechanical motion of the muscles.

Although only a few embodiments have been described in detail above, many modifications are possible and contemplated. For example, the shape of the chambers A and B can be modified to improve elastic characteristics and storage capacity of the pump. The chambers A and B need not be the same size and need not be cylindrical. Once optimized, each total segment can be arranged either in series or in parallel to change the working pressure or volume flux. The method of operation via pinching can be made asymmetric in order to provide a non-uniform displacement to achieve better performance. As alternatives to the pneumatic actuator, a linear motor or cam system can be used to actuate the segment P. Skeletal or artificial muscles could be used.

The tubes can be any material of tube, such as polyethylene, or body fluid resistant plastic. The "tubes" need not be round, but could be any shape cross section. Also, the reducing element could be any other structure which can change the fluidic characteristics asymmetrically.

All such modifications are intended to be encompassed within the following claims, in which:

What is claimed is:

1. A pump, comprising:
   first and second elastic chambers, said first elastic chamber having a first fluidic characteristic which is different than a second fluidic of characteristic said second elastic chamber; and
   a pressure increasing element, which induces a pressure increase into said first and second elastic chambers that causes a pressure difference between said first and second chambers that is based on said different fluidic characteristic differences of the chambers, to cause a pumping action based on said pressure difference.

2. A pump as in claim 1, wherein said fluidic characteristic is volume.

3. A pump as in claim 1, wherein said fluidic characteristic is length.

4. A pump as in claim 1, wherein said fluidic characteristic is size.

5. A pump as in claim 1, wherein said pressure increasing element is a volume reducing element.

* * * * *